(12) United States Patent
Vanotti et al.

(10) Patent No.: US 10,710,937 B2
(45) Date of Patent: Jul. 14, 2020

(54) EXTRACTION OF AMINO ACIDS AND PHOSPHORUS FROM BIOLOGICAL MATERIALS

(71) Applicant: The United States of America, as represented by the Secretary of Agriculture, Washington, DC (US)

(72) Inventors: Matias B. Vanotti, Florence, SC (US); Ariel A. Szogi, Florence, SC (US); Raul Moral Herrero, Alicante (ES)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/406,707

(22) Filed: May 8, 2019

(65) Prior Publication Data

US 2019/0263726 A1 Aug. 29, 2019

Related U.S. Application Data

(63) Continuation-in-part of application No. 16/180,287, filed on Nov. 5, 2018, which is a continuation of
(Continued)

(51) Int. Cl.
*C01B 25/04* (2006.01)
*C05B 17/00* (2006.01)
(Continued)

(52) U.S. Cl.
CPC .............. *C05B 17/00* (2013.01); *C01B 25/04* (2013.01); *C07K 1/145* (2013.01); *C12P 3/00* (2013.01); *C12P 21/00* (2013.01)

(58) Field of Classification Search
None
See application file for complete search history.

(56) References Cited

U.S. PATENT DOCUMENTS

| 4,897,266 A * | 1/1990 | Herve | A23L 17/60 |
| | | | 424/195.17 |
| 7,311,838 B2 * | 12/2007 | Herold | B01D 11/0288 |
| | | | 210/639 |

(Continued)

*Primary Examiner* — Melvin C. Mayes
*Assistant Examiner* — Colette B Nguyen
(74) *Attorney, Agent, or Firm* — John Fado; Ariel Atkinson

(57) ABSTRACT

A system and method for separating nutrients, such as phosphorus and protein, from biological materials may be disclosed. Biological material, for example in the form of wet solids from raw manure, may first be separated out by a solid-liquid separator. The wet solids may then be dissolved in an acidic solution, which may be created directly or by fermentation. The resulting supernatant from the acidic treatment may then be separated and phosphorus reclaimed therefrom. The resulting precipitate from the acidic treatment may be separated from the supernatant and treated with a basic solution. The resulting supernatant following the basic treatment may then be separated and protein reclaimed therefrom. In some embodiments, the supernatant resulting from the acidic treatment may itself be alkalinized, creating a precipitate which contains phosphorus solids and a supernatant which can be separated from the phosphorus solids and used as the basic solution with which to treat the precipitate resulting from the acidic treatment. Further, the system may be used to extract phosphorus and proteins from other biological materials, such as algae or crops.

23 Claims, 6 Drawing Sheets

Related U.S. Application Data application No. 15/350,283, filed on Nov. 14, 2016, now Pat. No. 10,150,711.

(51) Int. Cl.
  *C07K 1/14* (2006.01)
  *C12P 21/00* (2006.01)
  *C12P 3/00* (2006.01)

(56) References Cited

U.S. PATENT DOCUMENTS

| | | | |
|---|---|---|---|
| 7,431,841 B2 * | 10/2008 | Herold | B01D 11/0215 210/634 |
| 2001/0025820 A1 * | 10/2001 | Morse | C02F 1/24 210/724 |
| 2008/0053913 A1 * | 3/2008 | Fassbender | C02F 3/28 210/702 |
| 2010/0278973 A1 * | 11/2010 | Connell | A23K 10/14 426/53 |
| 2011/0089109 A1 * | 4/2011 | Ulmert | B01D 61/025 210/638 |
| 2015/0329399 A1 * | 11/2015 | Kumar | C05F 17/10 71/10 |
| 2016/0145164 A1 * | 5/2016 | Palmer | C05F 3/00 504/101 |

* cited by examiner

EXTRACTION OF AMINO ACIDS AND PHOSPHORUS FROM BIOLOGICAL MATERIALS

CROSS-REFERENCE TO RELATED APPLICATION

This application claims the benefit of U.S. Non-Provisional application Ser. No. 16/180,287, filed Nov. 5, 2018, which itself claims the benefit of U.S. Non-Provisional application Ser. No. 15/350,283 filed Nov. 14, 2016, now U.S. Pat. No. 10,150,711 both of which are incorporated herein by reference in their entireties.

BACKGROUND

This invention relates to systems and methods for extracting and recovering amino acids and phosphorus from animal and municipal wastes.

Municipal and agricultural waste disposal is a major problem. Feedlots, animal barns, agro-industrial plants, municipal sewage, and farms that keep large numbers of animals are sources of enormous quantities of organic waste. The disposal of untreated organic waste causes serious pollution problems which include those tied to the wastes' high content of chemically oxidizable components, expressed as COD or chemical oxygen demand, and BOD, biological or biochemical oxygen demand. When these pollutants reach bodies of water, either because they leach from disposal sites or as a consequence of being directly released or transported into water bodies, they deoxygenate the receiving waters and impair the receiving waters' capability to support aquatic life.

Acidity and high pathogen content add to the COD and BOD problems of untreated waste disposal. Acrid gases released into the atmosphere are not only unpleasant but they can also contribute to acid deposition, global greenhouse effects, and ozone depletion.

For agricultural animals, the animals are confined in high densities and lack functional and sustainable waste treatment systems. The liquid wastes are generally treated in large anaerobic lagoons with intermittent disposal through land applications (Stith, P. and Warrick, J., Boss Hog, North Carolina's pork revolution, The News & Observer, 1-3, Feb. 9-26, 1995; USEPA, Proposed regulations to address water pollution from concentrated animal feeding operations, EPA 833-F-00-016, January 2001, Office of Water, Washington, D.C., 20460). This system was developed in the early and mid-$20^{th}$ century prior to the current trend in high concentrated livestock operations. However, one of the problems with this approach is that recently there has been a push to reclaim nutrients from the manure for use as fertilizer, and the current approach is not sufficiently conducive to such a reclamation effort. In addition, when manure is stored in lagoons, runoff and leakage can detrimentally affect the water quality of rivers, lakes, and groundwater.

In particular, the recovery of phosphorus and proteins from manure could be advantageous to both offset costs and to improve and lessen the environmental impacts of manure storage and treatment. Phosphorous in manure can contaminate rivers, lakes, and bays through runoff, if applied onto a cropland excessively. Thus, recovering phosphorous from manure can not only help reduce such runoffs, but also reduces the use of commercial fertilizer based on phosphate rock. The phosphorus mine has limited reserves and cannot be replaced by other means as fertilizer. Protein is a natural resource used in a wide range of commercial applications from pharmaceuticals to dietary supplements, foods, feeds, and industrial applications.

All of the references cited herein, including U.S. patents and U.S. patent application Publications, are incorporated by reference in their entirety.

SUMMARY

According to at least one embodiment, a system and method for separating nutrients from biological materials may be disclosed. Biological material, for example in the form of wet solids from raw manure, may first be separated out by a solid-liquid separator. The wet solids may then be dissolved in an acidic solution. The resulting supernatant from the acidic treatment may then be separated and phosphorus reclaimed therefrom. The resulting precipitate from the acidic treatment may be separated from the supernatant and treated with a basic solution. The resulting supernatant following the basic treatment may then be separated and protein reclaimed therefrom. In some embodiments, the supernatant resulting from the acidic treatment may itself be alkalinized, creating a precipitate which contains phosphorus solids and a supernatant which can be separated from the phosphorus solids and used as the basic solution with which to treat the precipitate resulting from the acidic treatment. Further, the system may be used to extract phosphorus and proteins from other biological materials, such as algae or crops.

According to an alternative embodiment, a biological material may first be mixed with one or more sugars or sugar-containing mixtures and an inoculum and be allowed to ferment, thus creating an acidic solution. The sugar or sugar-containing mixture could include monosaccharides, such as glucose, fructose, mannose, and galactose; disaccharides such as sucrose, lactose, and maltose; polysaccharides that hydrolyze into fermentable sugars such as starch; molasses; fresh fruits or vegetables; fruit or vegetable waste; starch-rich materials such as potatoes, cassava, rice, maize, and their wastes; dairy materials containing lactose and their waste; mixtures of any of the above with a suitable solvent; and mixtures thereof. The inoculum may be any microbe, in either a cultured or dried form, which is capable of fermenting sugar to create an acidic product. Exemplary microbes include *Lactobacillus* sp. (*L. acidophilus, L. plantarum, L. casei, L. pentoaceticus, L. bulgaricus, L. brevis, L. thermophilus*), *Leuconostoc mesenteroides, Lactococcus* sp., and *Aspergillus niger.*

According to a further embodiment, the sugars or sugar-containing mixture may first be combined with the inoculum to form an acid precursor solution. Alternatively, the sugars or sugar containing mixture, the inoculum, and the biological material may be all combined at the same time.

BRIEF DESCRIPTION OF THE FIGURES

Advantages of embodiments of the present invention will be apparent from the following detailed description of the exemplary embodiments. The following detailed description should be considered in conjunction with the accompanying figures in which.

Exemplary

Exemplary

Exemplary

Exemplary

Exemplary

Exemplary

DETAILED DESCRIPTION

Figure 1:
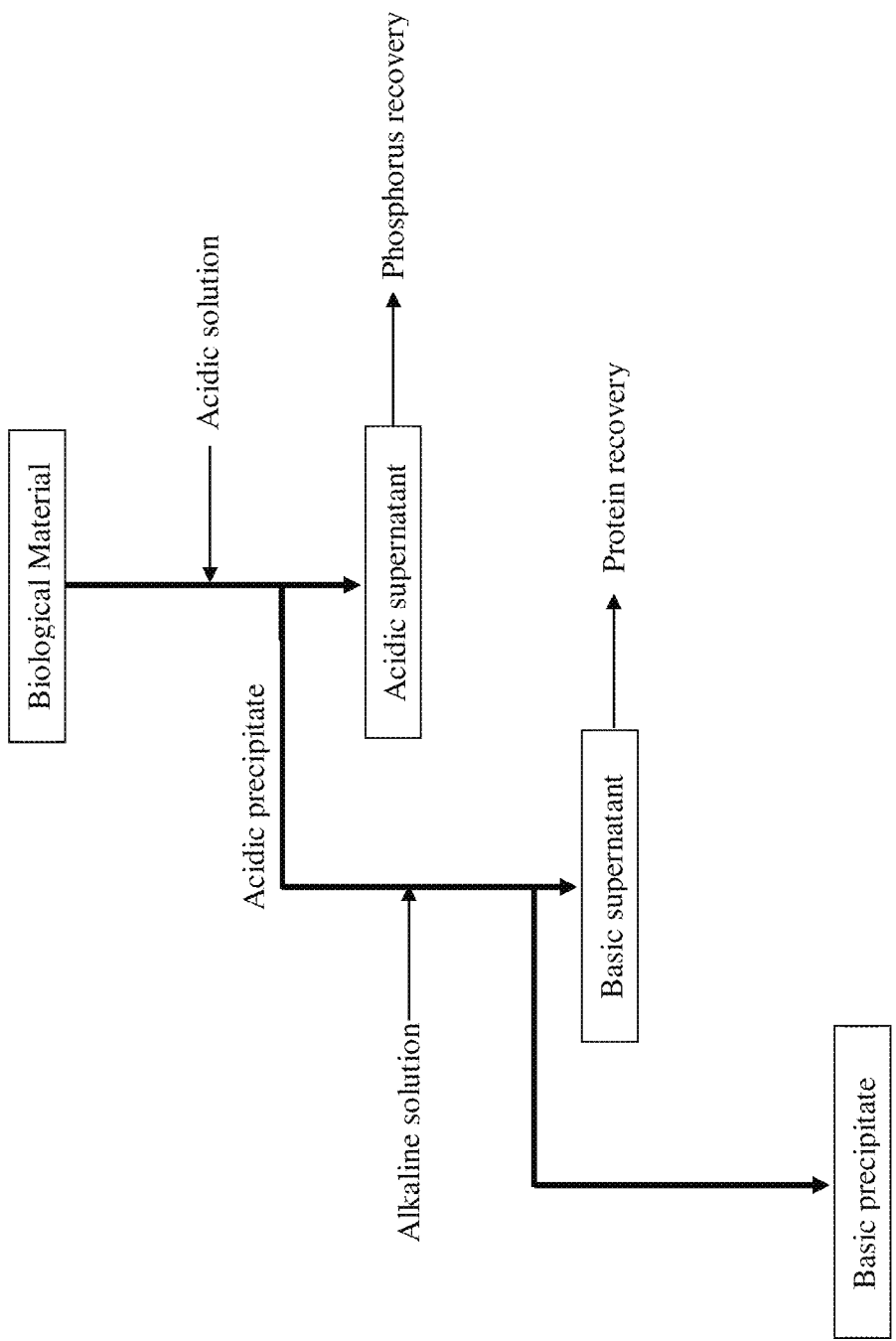
FIG. 1 shows an exemplary method of extracting phosphorus and protein from biological materials according to the present invention using a two-step process.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

"Biological material" means organic matter present or produced in a living organism. Non-limiting examples of biological materials include biomass from dead animals, animal waste, such as manure, biomass from dead plants, material cut off or grown by a living plant, and material derived directly from algae and bacteria, including bacterial and algae cells.

"Acid precursor" means a mixture or solution that contains at least one sugar and at least one microbe capable of fermenting said sugar, such that the acid precursor will, over time in appropriate conditions, become more acidic through fermentation of the sugar.

Other compounds may be added or used in the method provided they do not substantially interfere with the intended activity and efficacy of the method; whether or not a compound interferes with activity and/or efficacy can be determined, for example, by the procedures utilized below.

The amounts, percentages, and ranges disclosed herein are not meant to be limiting, and increments between the recited amounts, percentages, and ranges are specifically envisioned as part of the invention.

According to at least one embodiment, a system and method for separating nutrients from biological materials may be disclosed. Biological material, for example in the form of wet solids from raw manure, may first be separated out by a solid-liquid separator. The wet solids may then be dissolved in an acidic solution. The resulting supernatant from the acidic treatment may then be separated and phosphorus reclaimed therefrom. The resulting precipitate from the acidic treatment may be separated from the supernatant and treated with a basic solution. The resulting supernatant following the basic treatment may then be separated and protein reclaimed therefrom. In some embodiments, the supernatant resulting from the acidic treatment may itself be alkalinized, creating a precipitate which contains phosphorus solids and a supernatant which can be separated from the phosphorus solids and used as the basic solution with which to treat the precipitate resulting from the acidic treatment. Further, the system may be used to extract phosphorus and proteins from other biological materials, such as algae or crops.

Exemplary FIG. 1 shows an exemplary method for carrying out the present invention. Biological material may have an acidic solution added to it. After mixing, an acidic supernatant and acidic precipitate may be produced. Centrifuging may be used to easily separate the acidic supernatant from the acidic precipitate. Phosphorus recovery can then be completed from the acidic supernatant. The acidic precipitate may be mixed with an alkaline solution to produce a basic supernatant and basic precipitate. Centrifuging may be used to easily separate the basic supernatant from the basic precipitate. Protein recovery can then be completed from the basic supernatant and the basic precipitate may be disposed of.

Figure 2:
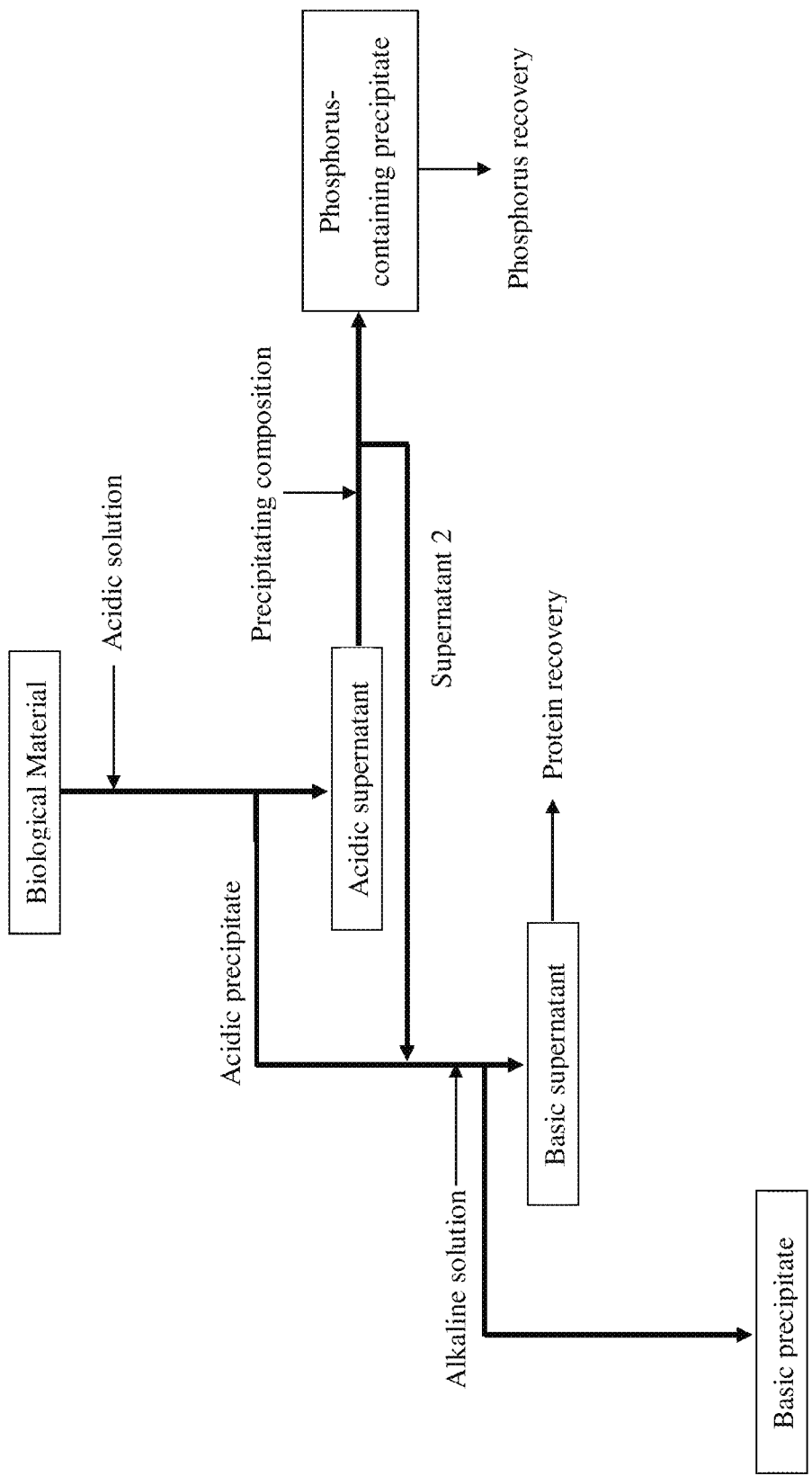
FIG. 2 shows an exemplary method of extracting phosphorus and protein from biological materials according to the present invention using a modified two-step process.

Exemplary FIG. 2 shows a second method for carrying out the present invention. Biological material may have an acidic solution added to it. After mixing, an acidic supernatant and acidic precipitate may be produced. Centrifuging may be used to easily separate the acidic supernatant from the acidic precipitate. A precipitating composition may be added to the acidic supernatant to cause a phosphorus-containing solid to precipitate. Centrifugation may then be used to separate a phosphorus-containing precipitate may from a second supernatant (labelled "Supernatant 2" in FIG. 2). The acidic precipitate may then be mixed with the second supernatant and an alkaline solution to produce a basic supernatant and a basic precipitate. Centrifuging may be used to easily separate the basic supernatant from the basic precipitate. Protein recovery can then be completed from the basic supernatant and the basic precipitate may be disposed of.

In the present invention, the biological material is not particularly limited. Examples of biological material may be animal waste such as manure, plant material such as ground and hydrated meal, and (re-)hydrated algae cells. It may be preferable for the biological material to be hydrated or wet prior to the initial acid extraction step.

The acid used in the acidic solution in the acid extraction step may be any suitable acid. Preferably, the acid is suitable for selectively precipitating proteins while keeping phosphorus in solution. Examples of acids useful in the present invention are mineral acids such as hydrochloric acid (HCl), sulfuric acid ($H_2SO_4$), nitric acid ($HNO_3$), and phosphoric acid ($H_3PO_4$), organic acids such as citric acid, oxalic acid, malic acid, fumaric acid, lactic acid, and EDTA, and mixtures thereof. The concentration of acid in the acidic solution may be from about 0.05 M to about 1.5 M. The acidic solution (solvent) may be added to the biological material in a ratio of 5 mL solvent per 1 g biological material to 20 mL solvent per 1 g biological material. Ratios of solvent to biological material use the equivalent dry weight of the biological material. For example, 5 g of wet manure may only contain 1 g of manure once dried. Thus, adding 10 mL of solvent to 5 g of wet manure may be exemplary of a 10 mL solvent:1 g manure (dry basis) ratio. The pH of the resulting mixture of acidic solution and biological material (process pH) may be from about 0.1 to about 6. Preferably, the pH may be from about 1 to less than 5.

The base used in the alkaline solution in the protein extraction step may be any suitable base. Preferably, the base is suitable for solubilizing proteins. Examples of bases which may be used in the present invention are sodium hydroxide (NaOH), calcium hydroxide ($Ca(OH)_2$), potassium hydroxide (KOH), magnesium hydroxide ($Mg(OH)_2$), or a mixture thereof. The concentration of base in the alkaline solution may be from about 0.1 M to about 1.0 M. The alkaline solution (solvent) may be added to the biological material in a ratio of 5 mL solvent per 1 g biological material to 20 mL solvent per 1 g biological material. Ratios of solvent to biological material use the equivalent dry weight of the biological material. For example, 5 g of wet manure may only contain 1 g of manure once dried. Thus, adding 10 mL of solvent to 5 g of wet manure may be exemplary of a 10 mL solvent:1 g manure (dry basis) ratio. The pH of the resulting mixture of alkaline solution and biological material (process pH) may be adjusted depending on the precipitating composition used, and may range from about 5 to about 14.

As stated above, a precipitating composition may be used in the present invention in an intermediary step. The precipitating composition may include one or more bases, such as those described above, a salt, and/or a flocculant. The salt may be any suitable salt. An example of a suitable salt may be calcium chloride ($CaCl_2$), magnesium chloride ($MgCl_2$), ferric chloride ($FeCl_3$), ferrous chloride ($FeCl_2$), aluminum chloride ($AlCl_3$), or a suitable mixture thereof. Further, the composition of the base(s) and/or salt(s) may be adjusted to control a ratio between the amount of the metal component of the salt (M) and phosphorus (P) in the mixture (M:P). The M:P ratio in the mixture may be between 0:1 and 3:1. Preferably, the M:P ratio may be between about 1:1 and about 2:1. For example, in the case of $CaCl_2$ being used as the salt, a Ca:P ratio of about 1.3 may be used. As stated above, the pH of the mixture of alkaline solution and biological material (process pH) may be adjusted depending on the precipitating composition used. For example, in the case of a calcium- or magnesium-containing salt, a pH of from about 11 to about 14. Preferably, the pH may be between 12 and 13. However, in the case of an iron-containing salt, the pH may preferably be between about 6.5 and about 7.5, and in the case of an aluminum-containing salt, the pH may preferably be between about 5 and about 7.

Flocculants may be used in the present invention to assist with separation of solids from liquid components of mixtures. For example, animal waste may be subjected to flocculation prior to the initial acid extraction step. Further, flocculation may be used to concentrate and precipitate one or both of phosphorus and proteins from the acidic and basic supernatants, respectively.

A method according to the present invention may involve one or more separations of centrifuged supernatants and precipitates. After initial separation of a supernatant and a precipitate, the precipitate may be washed, for example with water, to remove any latent supernatant. The resulting wash may then be added to the supernatant. Rinsing of the precipitate in this manner may be used any time a supernatant is separated from a precipitate. Rinsing may thus assist in more effectively separating the components dissolved in the supernatant from those in the precipitate and thus enhance separate recovery of nutrients.

Recovery of phosphorus and proteins from the acidic and basic supernatants, respectively, may be achieved through any suitable process. Separation of proteins may, for example be accomplished using ultra-filtration and freeze drying, acidic precipitation, and/or flocculation-assisted precipitation. According to at least one embodiment, the basic supernatant may be treated with an acid to bring the pH to below 6 to achieve acidic precipitation. According to another embodiment, the basic supernatant may be treated with a flocculant and with an acid to bring the pH to 4-4.5 to achieve flocculation and acidic precipitation of the protein. Preferably, the pH for acidic-assisted flocculation may be between about 4.2 and about 4.4.

Mixing methods in the present invention may involve any suitable and known mixing methods. For example, magnetic stirring rods, shakers, shaking tables, and/or dispersers may be used in the present invention. To assist with controlling foaming in mixing, a defoaming agent may be added to the mixture being mixed. For example, a defoamer or defoaming agent may be added when a disperser is used.

Separation of supernatants and precipitates may be accomplished by any known means. For example, centrifugation may be used to concentrate precipitates, as is known in the art. Other methods such as filtration, or any other suitable method may also be used.

Further illustration of the invention, its use, and its capabilities may be found in the following Examples:

Processing Manure with Alkaline Solution Only

One method for extracting potential nutrients from biological materials is to treat manure with an alkaline solution. Specifically, wet separated manure solids were mixed with an alkaline solvent in a ratio of 20 mL solvent:1 g manure. The alkaline solvent used was an aqueous solution of NaOH, and the molarity of NaOH in the solvent was varied from 0.025 M to 0.200 M. The wet solids and alkaline solvent were mixed using a magnetic stirrer and disperser (IKA T-18 Ultra Turrax) for 20 minutes and 10 minutes, respectively. The mixture was then centrifuged, and the resulting supernatant was analyzed for recoveries. The amount of protein recovered was determined by the Bradford method. The amount of phosphorus was determined using an Auto analyzer.

The results are shown in Table 1 below:

TABLE 1

| Solvent concentration of NaOH (M) | Process pH | % protein recovery | % phosphorus included with protein[1] |
|---|---|---|---|
| 0.025 | 9.5 | 33.5 | 10.0 |
| 0.050 | 10.2 | 34.4 | 10.7 |
| 0.075 | 11.0 | 37.2 | 15.5 |
| 0.100 | 12.0 | 49.0 | 17.0 |
| 0.125 | 12.4 | 71.4 | 33.5 |
| 0.150 | 12.7 | 83.2 | 44.1 |
| 0.175 | 12.9 | 91.0 | 42.8 |
| 0.200 | 13.0 | 100.5 | 45.7 |

[1]Represents the percent phosphorus compared to the total phosphorus in the original manure which was mixed in with the recovered protein.

As shown in Table 1, a higher concentration of NaOH, and thus higher process pH, leads to a higher recovery of protein. However, similarly as the solvent becomes more alkaline, a greater amount of phosphorus becomes included with the recovered protein. Thus, the above method may not be preferable as it does not lead to an efficient recovery and separation of both protein and phosphorus.

Processing Manure with Acidic and Alkaline Solutions

A second method to extract potential nutrients from biological materials is to treat wet manure first with an acidic solution and then after removing the supernatant, treating the resulting precipitate with an alkaline solution. According to this method, acidic solutions were prepared with both HCl and citric acid, with molarities of the dissolved acids ranging from about 0.2 to 0.6 to obtain a range of working pHs. In the first step, wet manure solids were mixed with the acidic solution, such as through methods including a magnetic stirrer and disperser as discussed above. The solvent/manure ratio used was 10 mL solvent:1 g manure. The mixture was then centrifuged, and the supernatant ("acidic supernatant") was separated from the precipitate ("acidic precipitate"). The acidic precipitate was then mixed with an alkaline solution (NaOH, 0.2 M) using the same method as above and centrifuged. The solvent/manure ratio used was 10 mL solvent:1 g manure. The resulting supernatant ("basic supernatant") was separated from the precipitate ("basic precipitate"). The acidic supernatant and basic supernatant were each individually analyzed for recoveries of protein and phosphorus (P).

The results are shown in Table 2 below:

TABLE 2

| Acid | pH of first step | pH of second step | % P[1] in AS[2] | % P in BS[1] | % Protein[1] in AS | % Protein in BS |
|---|---|---|---|---|---|---|
| HCl | 5.56 | 12.83 | 58.5 | 32.6 | 2.5 | 100 |
| HCl | 3.80 | 12.80 | 86.8 | 26.2 | 4.2 | 100 |
| HCl | 2.01 | 12.74 | 100.0 | 18.1 | 4.2 | 100 |
| HCl | 0.98 | 12.64 | 99.6 | 16.8 | 6.4 | 100 |
| Citric | 3.83 | 12.94 | 97.4 | 15.7 | 4.7 | 100 |
| Citric | 3.39 | 12.89 | 94.2 | 15.8 | 3.8 | 100 |
| Citric | 3.11 | 12.80 | 95.0 | 13.6 | 4.0 | 97.9 |
| Citric | 2.75 | 12.36 | 94.5 | 11.3 | 4.4 | 84.7 |

[1]% P and % Protein both refer to percentage recovery of each nutrient compared to the amount of nutrient in the original manure. The original manure contained 17.4% proteins and 2.69% P.
[2]"AS" and "BS" refer to acidic supernatant and basic supernatant, respectively.

Selectivity of NaOH Versus Ca(OH)$_2$

In a variant of the first method above, Ca(OH)$_2$ was substituted for NaOH to determine if the type of base had any effect on the results. Wet manure was mixed with the alkaline solvent. The alkaline solvent used was an aqueous solution of NaOH and/or Ca(OH)$_2$ in various proportions and the total molarity of bases in the solvent was kept constant at 0.67 M. The solvent/manure ratio used was 6 mL solvent:1 g manure (dry basis). The wet solids and alkaline solvent were mixed and centrifuged as described above, and the resulting supernatant was analyzed for recoveries.

The results are shown in Table 3 below:

TABLE 3

| NaOH, M | Ca(OH)$_2$, M | Total M | Process pH | % Protein[1] |
|---|---|---|---|---|
| 0.67 | 0.00 | 0.67 | 12.66 | 96.0 |
| 0.50 | 0.17 | 0.67 | 12.49 | 79.3 |
| 0.33 | 0.33 | 0.67 | 12.55 | 71.3 |
| 0.17 | 0.50 | 0.67 | 12.36 | 55.8 |
| 0.00 | 0.67 | 0.67 | 12.23 | 25.3 |

[1]Refers to percentage recovery of protein compared to the amount in the original manure.

Processing Manure with Acidic and Alkaline Solutions

To determine optimal conditions for the simultaneous extraction of protein and phosphorus from biological materials according to the present invention, several treatments (TRTs) were conducted to change different variables and study their effects. An initial determination was also made concerning the relative amounts of amino acids in the starting material, which was wet manure. The composition (% w/w) of amino acids relative to the total (dry) weight of the manure used in this experiment were alanine (1.09%); arginine (0.65%); asparagine and aspartic acid (1.51%); cysteic acid (0.31%); glutamine and glutamic acid (1.69%); glycine (0.88%); histidine (0.37%); isoleucine (0.89%); leucine (1.45%); lysine (0.89%); methionine sulfone (0.36%); phenylalanine (0.89%); proline (0.72%); serine (0.65%); threonine (0.78%); tryptophan (0.37%); tyrosine (0.76%); and valine (0.97%), for a total protein content of 15.17% (w/w).

TRT 1 was similar to the first method described above. An alkaline solution (0.4 N NaOH) was mixed with wet manure (10 mL: 1 g ratio, dry manure basis) via mixing and dispersing. The mixture was centrifuged and the percent protein recovered in the supernatant was determined.

TRT 2 was similar to the second method described above. In the first step (acid extraction), the acidic solution (citric acid, 0.2 M) was mixed with wet manure (10 mL: 1 g ratio, dry manure basis) via mixing and dispersing. The mixture was centrifuged to obtain an acidic supernatant and acidic precipitate. In the second step (protein extraction), the acidic precipitate was mixed with the alkaline solution (NaOH, 0.6 N) via mixing and dispersing. The mixture was centrifuged to obtain a basic supernatant and basic precipitate. The acidic supernatant was then analyzed for phosphorus recovery and the basic supernatant was analyzed for protein recovery.

TRT 3 was conducted in the exact same manner as TRT 2, except that the alkaline solution was NaOH, 0.4 N.

TRT4 involved first conducting an acid extraction by mixing an acidic solution (citric acid, 0.2 M) with wet manure (10 mL: 1 g ratio, dry manure basis) as described above in the amounts of 20 mL of acidic solution and 2 g (dry basis) of manure, and then centrifuged to obtain a first supernatant (the acidic supernatant) and acidic precipitate. Then a phosphorus precipitation was conducted by adding a precipitating composition to the acidic supernatant. The precipitating composition was 2.75 mL of 4 N NaOH$_{aq}$ and 0.1648 g CaCl$_2$. The amount of CaCl$_2$) added meant that there was about a 1:1 molar ratio of Ca:P in the resulting solution. In addition, 1 mL of 0.5% flocculant was added to assist with the phosphorus precipitation. The resulting mixture was mixed and then centrifuged to obtain a phosphorus-containing precipitate and a second supernatant. The second supernatant was then mixed with the acidic precipitate and an alkaline solution (NaOH 0.4) to conduct a protein extraction. The mixture was mixed and centrifuged to obtain a third supernatant (basic supernatant) and a basic precipitate. The phosphorus-containing precipitate and the third supernatant were then analyzed for phosphorus and protein recoveries, respectively.

TRT 5 was the same as TRT 4, except that the amount of $CaCl_2$) added in the phosphorus precipitation was 0.3296 to double the Ca:P ratio to about 2:1.

TRT 6 was the same as TRT 4, except that the acidic solution in the acid extraction was 0.117 M citric acid and the amount of 4 N NaOH in the precipitating composition was 2 mL.

TRT 7 was the same as TRT 6, except that the amount of $CaCl_2$) added in the phosphorus precipitation was 0.3296 to double the Ca:P ratio to about 2:1.

TRT 8 was the same as TRT 4, except that the precipitating composition was only 2 mL of 14.8% $Ca(OH)_2$ thus providing a Ca:P molar ratio of 2.69:1, only 0.5 mL of flocculant was used in the phosphorus precipitation, and the alkaline solution used in the protein extraction was 0.6 N NaOH.

TRT 9 was the same as TRT 8, except that no flocculant was used.

TRT 10 was the same as TRT 6, except that the precipitating composition was only 1 mL of 14.8% $Ca(OH)_2$ thus providing a Ca:P molar ratio of 1.35:1, and only 0.5 mL of flocculant was used in the phosphorus precipitation.

TRT 11 was the same as TRT 10, except that no flocculant was used.

The results of the above treatments (TRTs) 1-11 are shown in Table 4 below:

culant (Magnafloc 120 L, BASF Corp.) in amounts of 120 mg/L and 180 mg/L, respectively. HCl was then added to the flocculant-treated portions to bring the pH further down to 4.4 where flocculation and precipitation was observed. The mixtures were then centrifuged to determine the results of flocculant-assisted precipitation.

The results are shown in Table 5 below:

TABLE 5

| Treatment | solution pH | | protein concentration (g/L) | | Protein precipitation efficiency (%) |
|---|---|---|---|---|---|
| | Initial[1] | Final | Initial | Final | |
| Acid and no flocculant | 11.9 | 5.5 | 8.14 | 1.98 | 75.6 |
| Acid and 120 mg/L flocculant | 11.9 | 4.4 | 8.14 | 1.62 | 80.1 |
| Acid and 180 mg/L flocculant | 11.9 | 4.4 | 8.14 | 0.66 | 91.8 |

[1]This is the starting pH of the protein solution prior to the addition of HCl.

In addition, it was found that flocculation only occurred in a narrow pH band of 4.2-4.4. Solutions with a pH of less than 4 caused the flocs to disappear (redissolve).

Processing Other Biological Materials

Soybean meal and *spirulina* algae were both subjected to acid and alkaline extractions as described below:

Soybean meal for animal feed was obtained from Elgin Feed and Gardens (SC). First an acid extraction was conducted by mixing the meal with an acidic solution (HCl or

TABLE 4

| TRT | Acid Extraction pH | Phosphorus precipitation | | | | | | Recoveries | | |
|---|---|---|---|---|---|---|---|---|---|---|
| | | 4N NaOH (mL) | $CaCl_2$ (g) | 14.8% $Ca(OH)_2$ (mL) | Ca:P molar ratio | 0.5% flocculant (mL) | pH | Protein Extraction pH | % P recovery | % Protein recovery |
| 1 | — | — | — | — | — | — | | 12.40 | — | 132.6 |
| 2 | 3.83 | — | — | — | — | — | | 12.77 | 90.6 | 136.1 |
| 3 | 3.84 | — | — | — | — | — | | 12.41 | 84.8 | 116.2 |
| 4 | 3.77 | 2.75 | 0.1648 | 0 | 1:1 | 1 | 12.27 | 12.51 | 87.7 | 105.1 |
| 5 | 3.72 | 2.75 | 0.3296 | 0 | 2:1 | 1 | 12.35 | 12.32 | 87.7 | 89.4 |
| 6 | 4.77 | 2 | 0.1648 | 0 | 1:1 | 1 | 12.50 | 12.97 | 107.2 | 123.8 |
| 7 | 4.70 | 2 | 0.3296 | 0 | 2:1 | 1 | 12.25 | 12.88 | 100.5 | 123.1 |
| 8 | 3.80 | 0 | 0 | 2 | 2.69:1 | 0.5 | 8.75 | 12.64 | 87.7 | 78.8 |
| 9 | 3.84 | 0 | 0 | 2 | 2.69:1 | 0 | 8.99 | 12.69 | 87.7 | 93.7 |
| 10 | 4.77 | 0 | 0 | 1 | 1.35:1 | 0.5 | 8.94 | 12.51 | 104.0 | 88.4 |
| 11 | 4.69 | 0 | 0 | 1 | 1.35:1 | 0 | 8.92 | 12.31 | 113.6 | 98.2 |

Concentration of Protein in Basic Supernatant

Exemplary embodiments of the invention may include the concentration and precipitation of protein in the basic supernatant using acid and/or a flocculant to ease in the recovery of the protein component. To study this, wet manure was first subjected to an acid extraction using 0.33 M citric acid in a 6 mL:1 g solvent:dry manure basis. The resulting acidic precipitate was then subjected to a protein extraction using 0.668 N NaOH. The resulting basic supernatant was the protein solution used in this study.

The protein solution was first acidified to a pH of 5.5 through the addition of HCl. A portion of this mixture was then centrifuged to determine the results of acid-only precipitation. Two other portions were each treated with floccitric acid, 0.4 M-1.2 M) in a solvent to meal ratio of 10 mL solvent:1 g meal. The mixture was mixed and centrifuged to obtain an acidic supernatant and acidic precipitate. The acidic precipitate was treated with an alkaline solution (NaOH) to conduct the protein extraction. The mixture was mixed and centrifuged to obtain a basic precipitate and basic supernatant. The acidic supernatant and basic supernatant were analyzed for phosphorus and protein recoveries, respectively.

Dried *spirulina* algae was first hydrated with water overnight. Then an acid extraction was conducted by mixing the hydrated algae with acidic solution (HCl or citric acid, 0.05 M-1.2 M) in a solvent to meal ratio of 10 mL solvent:1 g dry algae. The mixture was mixed and centrifuged to obtain an acidic supernatant and acidic precipitate. The acidic precipitate was treated with an alkaline solution (NaOH) to conduct the protein extraction. 0.6 mL of a defoamer solution was also added to the mixture. The mixture was mixed and centrifuged to obtain a basic precipitate and basic supernatant. The acidic supernatant and basic supernatant were analyzed for phosphorus and protein recoveries, respectively.

The results are shown in Table 6 below:

TABLE 6

| Starting material | Acid type | Phosphorus recovery | | Protein recovery | |
|---|---|---|---|---|---|
| | | pH | % P recovered | pH | % protein recovered |
| Soybean meal | Citric | 2.53 | 19.0 | 12.77 | 74.0 |
| Soybean meal | Citric | 2.13 | 19.4 | 12.81 | 64.7 |
| Soybean meal | Citric | 1.88 | 22.9 | 12.79 | 46.4 |
| Soybean meal | HCl | 0.80 | 73.6 | 12.94 | 85.3 |
| Soybean meal | HCl | 0.38 | 86.1 | 12.94 | 95.7 |
| Soybean meal | HCl | 0.17 | 92.0 | 12.85 | 88.2 |
| Algae | Citric | 4.2 | 75.7 | 12.94 | 82.9 |
| Algae | Citric | 3.61 | 88.9 | 12.75 | 86.1 |
| Algae | Citric | 3.08 | 87.1 | 12.84 | 103.5 |
| Algae | Citric | 2.60 | 82.6 | 12.83 | 98.4 |
| Algae | Citric | 2.33 | 74.0 | 12.70 | 83.0 |
| Algae | Citric | 2.07 | 76.6 | 12.90 | 76.2 |
| Algae | HCl | 3.59 | 93.0 | 12.94 | 77.3 |
| Algae | HCl | 1.87 | 87.2 | 12.72 | 79.8 |
| Algae | HCl | 0.84 | 81.1 | 12.78 | 71.1 |
| Algae | HCl | 0.51 | 70.3 | 12.97 | 94.4 |
| Algae | HCl | 0.31 | 80.2 | 13.06 | 96.0 |

Use of Sugars and Fermentation to Achieve Acidic Solution

Figure 3:
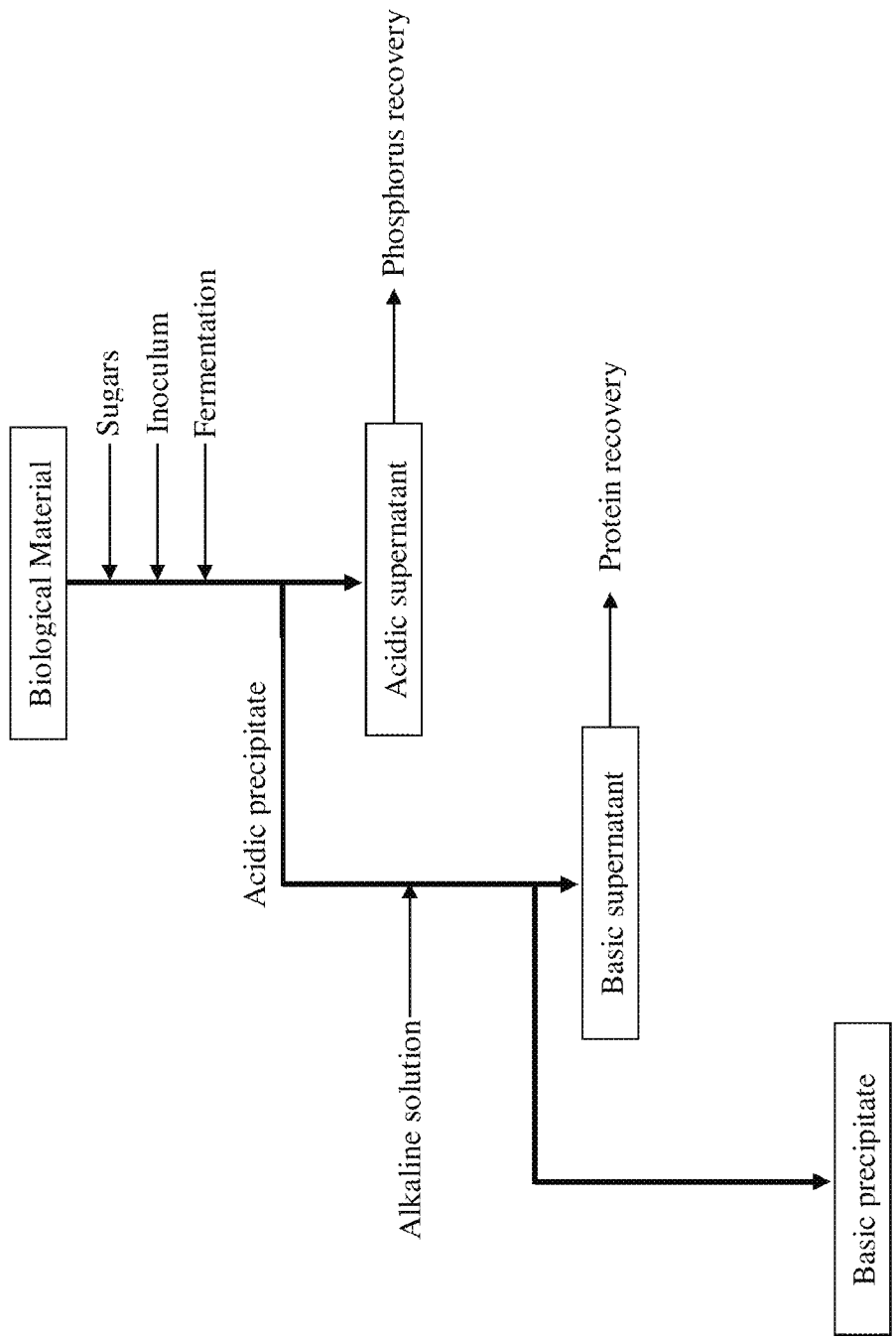
FIG. 3 shows an exemplary method of extracting phosphorus and protein from biological materials according to the present invention using a three-step process.

As an alternative to the two-step methodologies explained above where an acid solution is added first and an alkaline solution second, a three-step method may be used in which a sugar or sugar-containing mixture is added to the biological material together with an inoculum, and a fermentation step is taken to acidify the mixture prior to separation of the acidic supernatant and precipitate (see FIG. 3). It is noted that though FIG. 3 shows a method which is directly analogous to FIG. 1, however the substitution of sugar, inoculum, and fermentation could be used in the method shown in FIG. 2 as well, as one of skill in the art would understand.

Sucrose. To provide a proof-of-concept, sucrose and *Lactobacillus acidophilus* were mixed together with wet separated swine manure and fermented. First an *L. acidophilus* suspension was prepared by dissolving 3 tablets of *L. acidophilus* (1.1 g total; 1.5 billion CFU) (*Acidophilus* Probiotics, Nature Made Nutritional Products, Mission Hills, Calif.) in 25 mL of water. The mixture was centrifuged, and the supernatant decanted and discarded. Then 20 mL of water was added to the remaining solids to create the *L. acidophilus* suspension. An acid precursor was created by dissolving different amounts of sucrose (A.C.S., Fisher Scientific) in 19 mL of water, and then adding 1 mL of the *L. acidophilus* suspension to the sucrose solution. The amounts of sucrose dissolved were 0, 0.5, 0.75, 1.0, 1.5, and 2.0 g. The manure used in each case was 10.8 g wet manure (2.0 g dry basis).

The acid precursor solutions were mixed with the manure in a ratio of 10:1 precursor to manure (dry manure basis) to create fermentation mixtures. The fermentation mixtures were then incubated at 37° C. in closed vessels with slow agitation for about 30 hours. The mixtures were then centrifuged, and the acidic supernatant was separated from the acidic precipitate. The acidic precipitates were subjected to a water rinse by mixing the acidic precipitate with water using a volume of water similar to the initial precursor solution volume (20 mL). The mixtures were then centrifuged, and the rinse supernatant was separated from the rinsed acidic precipitate and combined with the first acidic supernatant to form a combo acidic supernatant. Further processing of the rinsed acidic precipitate was carried out as described above using an alkaline solution (0.4 M NaOH) to conduct protein extraction. Table 7 below shows the results from these tests:

TABLE 7

| Sucrose treatment | pH of first step | pH of second step | % P[1] in AS[2] | % P in BS[2] | % Protein[1] in AS | % Protein in BS |
|---|---|---|---|---|---|---|
| 0.00 g | 7.07 | 13.43 | 10.8 | 74.3 | 4.1 | 80.1 |
| 0.50 g | 5.30 | 13.50 | 65.4 | 39.1 | 4.7 | 93.6 |
| 0.75 g | 4.76 | 13.51 | 81.9 | 33.9 | 4.4 | 101.3 |
| 1.00 g | 4.45 | 13.46 | 80.6 | 28.3 | 3.3 | 103.8 |
| 1.50 g | 4.21 | 13.49 | 79.6 | 28.8 | 3.0 | 106.4 |
| 2.00 g | 4.22 | 13.44 | 84.7 | 31.0 | 4.0 | 110.8 |

[1] % P and % Protein both refer to percentage recovery of each nutrient compared to the amount of nutrient in the original manure. The original manure on dry basis contained 15.17% proteins and 2.9% P.
[2] "AS" and "BS" refer to acidic supernatant and basic supernatant, respectively.

The above results suggest that very little sugar is required to gain significant phosphorous and protein recovery. After the short fermentation of the manure with 0.75 and 1.0 g of sucrose, the pH decreased from 8.3 to about 5 to 4.5 which was highly effective to both solubilize the phosphorus and precipitate proteins. Although as little as 0.75 g of sucrose achieved over 80% recovery of phosphorous in the acidic supernatant, even 0.5 g of sucrose saw 65% recovery. It is likely that measurable recovery may be achieved with even less sucrose, though it would not be as desirable as the recovery would decrease with a less acidic solution. Further, the results indicate that when sugars were added the fermentation time did not adversely affect the proteins, as they were still recoverable in the basic supernatant. However, without sugar addition, the fermentation time adversely affected the proteins because acidified conditions were not developed (pH 7.07) which reduced protein recovery by approximately 20%.

Molasses. To test other sugar sources, molasses was used. Beet molasses was used in place of the sucrose in the above method. The beet molasses (Midwest Agri, Caro, Mich.) had the following characteristics: Brix 81.48 deg, pH 7.4, polarity 46.94, and purity 58.82% (wt/wt). Experiments were carried out using 0, 0.5, 0.75, 1.0, 1.5, and 2.0 g of molasses in place of the sucrose. All other variables and conditions were the same. The results are shown in Table 8 below:

TABLE 8

| Molasses treatment | pH of first step | pH of second step | % P[1] in AS[2] | % P in BS[2] | % Protein[1] in AS | % Protein in BS |
|---|---|---|---|---|---|---|
| 0.00 g | 6.81 | 13.29 | 12.3 | 45.2 | 5.8 | 88.6 |
| 0.50 g | 5.83 | 13.29 | 38.1 | 30.4 | 8.2 | 90.4 |

TABLE 8-continued

| Molasses treatment | pH of first step | pH of second step | % P[1] in AS[2] | % P in BS[2] | % Protein[1] in AS | % Protein in BS |
|---|---|---|---|---|---|---|
| 0.75 g | 5.45 | 13.29 | 62.3 | 23.5 | 8.5 | 96.0 |
| 1.00 g | 5.03 | 13.32 | 73.3 | 18.9 | 8.7 | 98.5 |
| 1.50 g | 4.61 | 13.35 | 81.8 | 15.8 | 7.6 | 103.1 |
| 2.00 g | 4.40 | 13.35 | 82.1 | 14.5 | 8.5 | 99.2 |

[1]% P and % Protein both refer to percentage recovery of each nutrient compared to the amount of nutrient in the original manure. The original manure on dry basis contained 15.17% proteins and 2.9% P.
[2]"AS" and "BS" refer to acidic supernatant and basic supernatant, respectively.

The results above demonstrate that molasses is an effective sugar source for the acid precursor. Though not as effective gram-for-gram, some phosphorous recovery was still achieved even with as little as 0.5 g of molasses. However, at least 1.0 g of molasses may be more desired to achieve at least 73% recovery of phosphorous. Further, the molasses fermentation did not adversely affect the protein recovery.

Fruit. In addition, fruit was tested as a natural product that could be used as a sugar source for the present process. Both fresh and waste peaches were tested. For fresh peaches, the peaches were pitted, cut peaches were placed in a food processer to "liquify" them, and then the acid precursor mixtures were created according to the treatments listed in Table 9 below. The liquified fresh peaches contained the following (per 100 g fresh weight): 90.4 g moisture, 9.6 g total solids, 8.5 g volatile solids, 7.85 g total sugars (1.78 g fructose, 2.03 g glucose, 4.04 g sucrose), 198.0 mg malic acid and 96.6 mg citric acid, 185 mg proteins, 16.7 mg P, 8.9 mg Ca, and 6.1 mg Mg. The fresh peaches had a pH of 3.77, a titratable acidity of 9.60 meq per 100 g peach (acidity to pH 8.1, AOAC method 942.15), and a Brix of 7.7 deg.

TABLE 9

| Treatment/amount of peaches | Water | Acidophilus Solution |
|---|---|---|
| 0.0 g | 30 mL | 1 mL |
| 7.5 g | 22.5 mL | 1 mL |
| 15.0 g | 15.0 mL | 1 mL |
| 22.5 g | 7.5 mL | 1 mL |
| 30.0 g | 0.0 mL | 1 mL |

The acid precursors were mixed with the manure in a ratio of 10:1 precursor to manure and incubated at 37° C. with slow agitation for about 24 hours. The mixtures were then processed as described above. The results are shown in Table 10 below:

TABLE 10

| Peaches treatment | pH of first step | pH of second step | % P[1] in AS[2] | % P in BS[2] | % Protein[1] in AS | % Protein in BS |
|---|---|---|---|---|---|---|
| 0.0 g | 7.51 | 13.13 | 17.6 | 73.8 | 6.8 | 87.1 |
| 7.5 g | 5.98 | 13.19 | 53.5 | 32.8 | 7.0 | 87.7 |
| 15.0 g | 5.32 | 13.23 | 71.1 | 23.2 | 5.3 | 91.3 |
| 22.5 g | 5.05 | 13.07 | 81.0 | 21.6 | 4.8 | 89.6 |
| 30.0 g | 4.86 | 13.01 | 81.8 | 19.5 | 3.9 | 81.3 |

[1]% P and % Protein both refer to percentage recovery of each nutrient compared to the amount of nutrient in the original manure and peaches. On a dry basis, the original manure contained 15.17% proteins and 2.9% P. At the highest treatment, the peach material added 12.4% and 5.7% to the amount of protein and P in the original manure, respectively.
[2]"AS" and "BS" refer to acidic supernatant and basic supernatant, respectively.

The pH of the fermentation mixture was decreased with increased rates of peaches. There were two pH decreases of the manure. First there was an instant pH decrease due to the inherent acidity of the peach material (9.60 meq per 100 g peach), from 8.38 in the original manure to 8.13, 7.27, 6.86, 6.61 and 6.29 in the 0, 7.5, 15, 22.5 and 30 g peach treatments. Then there was a second decrease due to the fermentation of sugars contained in the peach (7.5 g total sugars/100 g peach) needed to lower the pH to levels about 5 or below that are most effective for phosphorus recovery (Table 10). The following organic acids were found in the acidic supernatant, as measured in the 30 g peach treatment (mg per 100 g of liquid): lactic acid 1195 mg, citric acid 119.5 mg, and malic acid <40.0 mg.

The results above demonstrate that fresh peaches are an effective sugar source for the acid precursor. Some phosphorous recovery was still achieved even with as little as 7.5 g of peaches. However, at least 15.0 g of peaches may be more desired to achieve at least 71% recovery of phosphorous. Further, the peach fermentation did not adversely affect the protein recovery.

It is appreciated that peaches are not the sole fruit or food product (i.e. vegetables) that contains significant amounts of sugar. It is contemplated that other sugar-containing agricultural products such as other fruits and vegetables could be used in the present invention for the same purpose with minor adjustments for amounts depending on the sugar concentration and initial pH of the fruit or vegetable.

Fruit Waste.

An experiment was also conducted with waste peaches (peaches that were too soft, had bad spots, or did otherwise not meet the grade for sale as fresh fruit). The waste peaches were obtained from McLeod Farms Processing Plant, McBee, S.C. The experiment was run using the same mixture ratio as the 30 g fresh peach treatment above, with all other variables constant except that the fermentation was conducted for 48 hours. The waste peaches contained the following (per 100 g fresh weight): 89.8 g moisture, 10.2 g total solids, 9.4 g volatile solids, 8.41 g total sugars (1.78 g fructose, 2.27 g glucose, and 4.35 g sucrose), 194.5 mg malic acid, 74.4 mg citric acid, 222 mg proteins, 17.2 mg P, 8.1 mg Ca, and 6.0 mg Mg. The waste peaches had a Brix of 7.7 deg, pH of 3.76, and a titratable acidity of 9.63 meq per 100 g peach (acidity to pH 8.1, AOAC method 942.15).

Figure 4:
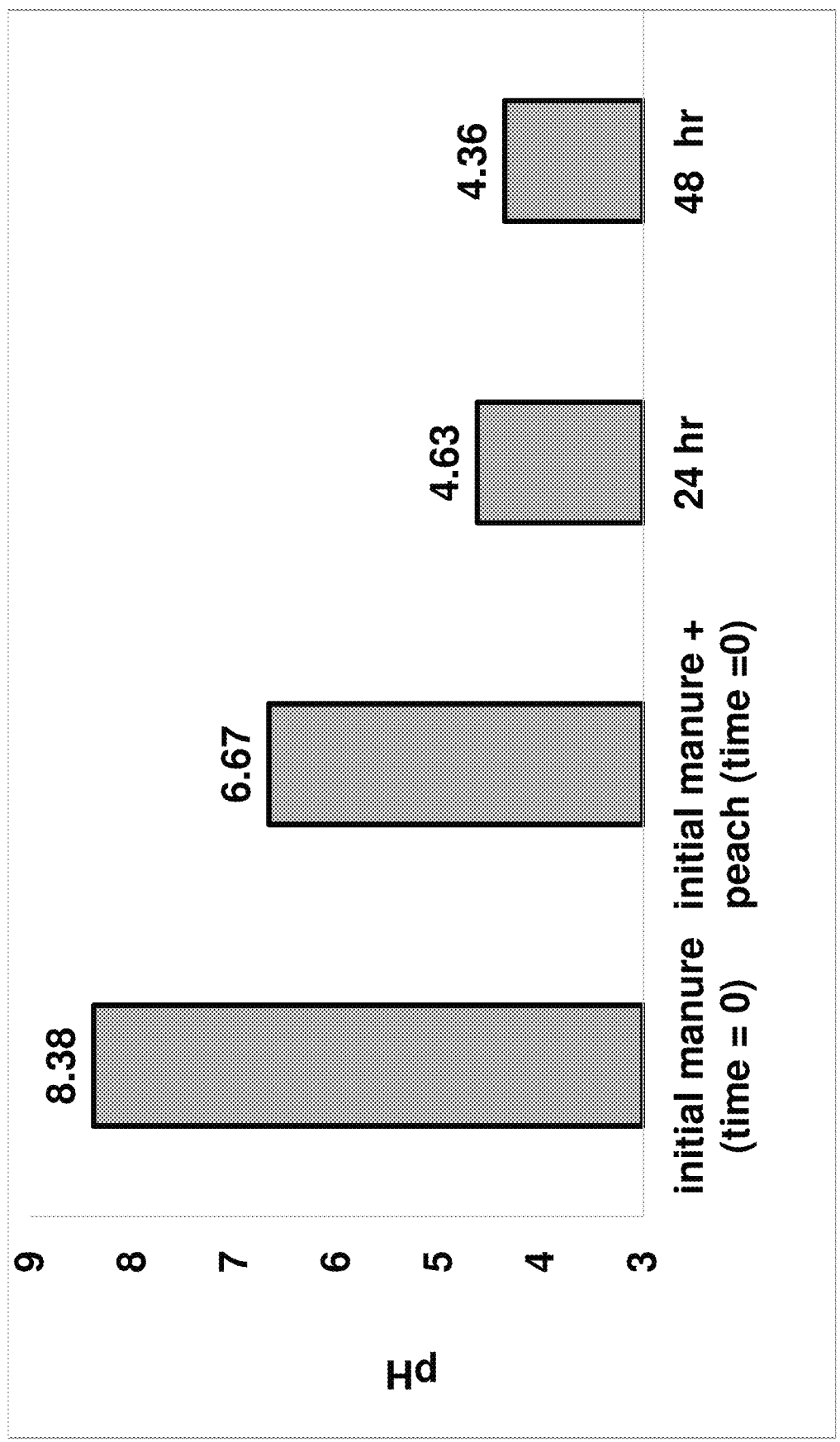
FIG. 4 shows pH of manure mixtures immediately after adding peaches and after 24-48 hours of fermentation.

Due to the natural acidity of the waste peaches, the pH of the manure dropped instantly from 8.38 to 6.67 after addition of the waste peaches. However, for effective phosphorus extraction, a pH less than 6 is desired. These conditions were achieved after rapid fermentation: the pH of the mixture further dropped to pH 4.63 after a fermentation period of 24 hours, and to pH 4.36 after 48 hours (FIG. 4). The recovery rates were 74.4% phosphorous in the acid supernatant, 24.5% phosphorous in the basic supernatant, 2.7% protein in the acid supernatant, and 96.6% protein in the basic supernatant. Further experiments for phosphorus recovery using above-described methods (for example those used in Treatment 4 (TRT 4) in Table 4, but using either $Ca(OH)_2$ or a mixture of NaOH and $MgCl_2$ as the phosphorus precipitating solution) demonstrated that such methods are also effective for phosphorus recovery with using fruit waste and an acid precursor (data not shown).

Thus, fruit waste, an abundant waste product, can also be effectively used as a sugar source for this process.

Comparison of Sucrose, Molasses, and Fruit.

Figure 5:
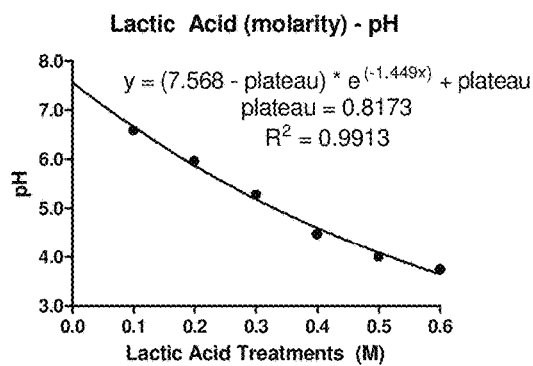
FIG. 5 shows pH graphs of the acidification of manure using lactic acid and comparisons with sugar sources.
Figure 5:
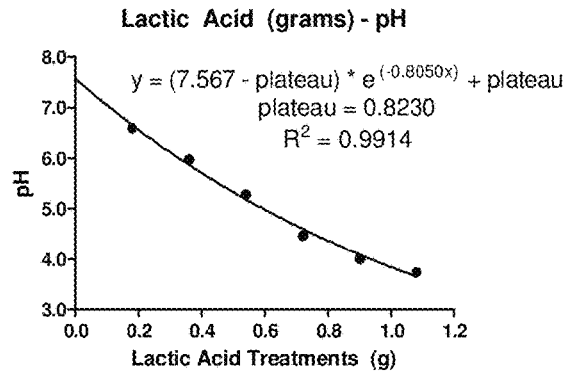
Figure 5:
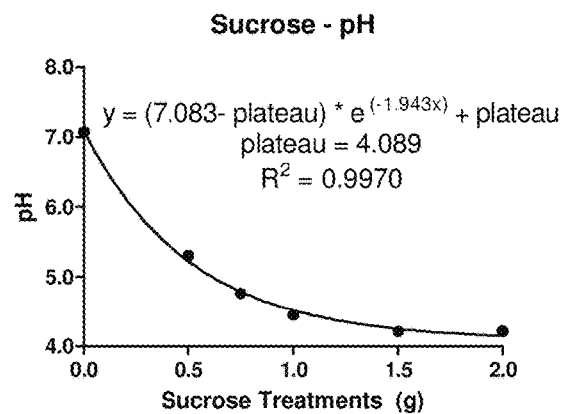
Figure 5:
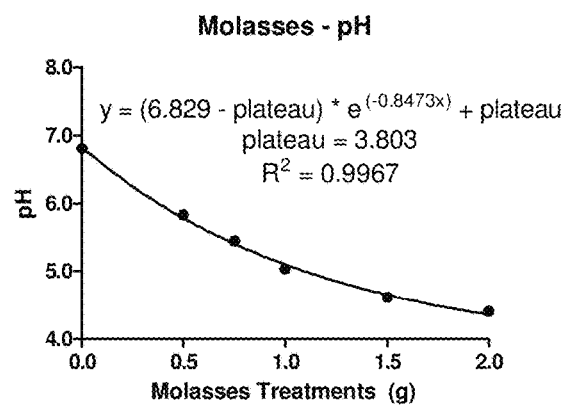
Figure 5:
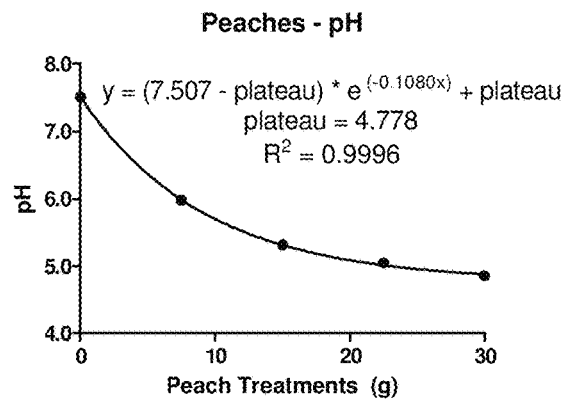

Data in FIG. 5 compares the pH decrease of the manure solids by the various acid precursors and fermentation described in the previous experiments (sucrose, molasses and peach experiments) vs. the pH decrease by addition of pure lactic acid without fermentation (lactic acid was chosen in the comparison because it was the principal acid found in the acidic supernatant after fermentations). Six lactic acid treatments were added to the manure in 20 mL solutions containing 0.1, 0.2, 0.3, 0.4, 0.5 and 0.6 moles per L lactic acid (0.18, 0.36, 0.54, 0.72, 0.90 and 1.08 g lactic acid) in a 10:1 solution to manure ratio (manure dry basis). All other variables and conditions were the same (the exception in the comparisons is that peach treatments were added to 50% more manure (3 g dry basis vs. 2 g). Lactic acid treatments of 0.72 g lowered the manure pH to 4.57. This acidification compares to the effect of about 0.75 to 1 g sucrose treatment using the fermentation route (pH 4.76 to 4.45), or to the effect of 1.0 to 1.5 g of molasses treatment (pH 5.03 to 4.61), or to the effect of 22.5 to 30 g fresh peaches that are about 90% water (pH 5.05 to 4.86).

Figure 6:
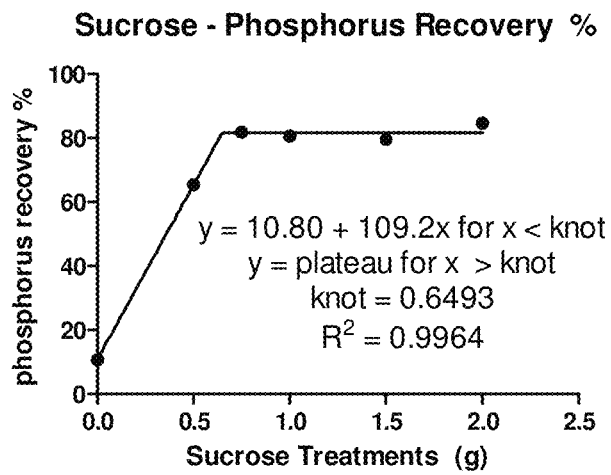
FIG. 6 shows phosphorus recovery plots for different amounts of sugar sources.
Figure 6:
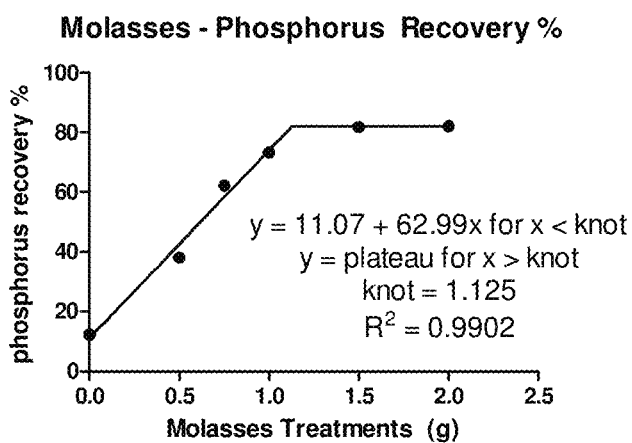
Figure 6:
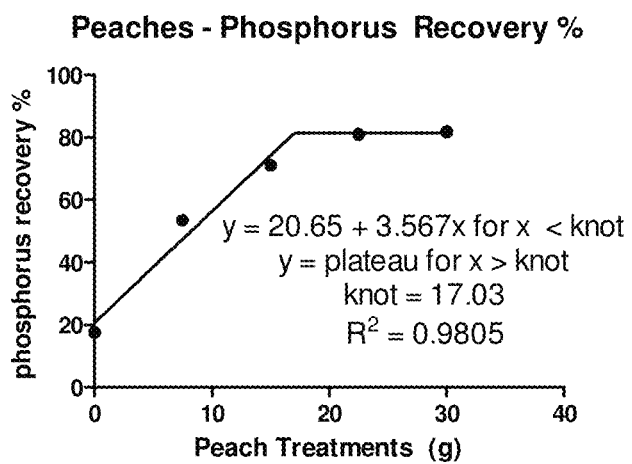

A one phase decay model fit the data well ($R^2>0.99$). The model, $\{Y=[(Yo-plateau)*e^{(-k \cdot x)}]+plateau\}$, contains an Intercept (Yo) that is the pH value when the treatment rate (X) is zero, a Plateau that is the lowest pH at infinite treatment rate, and a rate constant (k). The Span is the difference between Yo and plateau, and represents the potential pH drop in the manure mixture with fermentation after adding an acid precursor material in non-limited amounts. The Spans thus obtained were consistent across the variety of acid precursors tested: 2.99 pH units for sucrose, 3.02 pH units for molasses, and 3.03 pH units for peaches. This suggests that the activity of the acid-producing microorganisms is halted after reaching similar low acidity levels. However, for maximizing phosphorus recovery, lower precursor rates are needed. The phosphorus recovery data were fitted to a linear plateau model ($R^2>0.98$) (FIG. 6). There was a sustained increase in phosphorus recovery up to a "knot" value representing the lower precursor rate that first maximized phosphorus recovery. Increased rates above the knot value did not increase or decrease phosphorus recovery (plateau % phosphorus recovery). The lower treatments rates that optimized P recovery were: 0.65 g for sucrose, 1.12 g for molasses, and 17.0 g for peaches (11.3 g when adjusted to same manure amount used in the other treatments). When these optimum precursor rate values are used to solve Y in the corresponding pH curve equations (FIG. 5), the pH values obtained were: 4.94 for fructose, 4.97 for molasses, and 5.21 for peaches. Therefore, without being bound by theory, it appears that a pH of about 5 or less than 5 is a useful target to optimize the P recovery step using acid precursors.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for separating phosphorus and protein from biological materials, comprising:
   conducting an acid extraction by mixing together (a) a sugar or a sugar-containing mixture, (b) an inoculum, and (c) a biological material to create a fermentation mixture, then conducting a fermentation process to acidify the fermentation mixture, to produce an acidic supernatant and an acidic precipitate;
   separating the acidic supernatant from the acidic precipitate;
   conducting a protein extraction by adding an alkaline solution to the acidic precipitate and mixing the alkaline solution with the acidic precipitate to produce a basic supernatant and a basic precipitate;
   separating the basic supernatant from the basic precipitate; and
   recovering an amount of phosphorus from the acidic supernatant and recovering an amount of protein from the basic supernatant.

2. The method according to claim 1, wherein the biological material is one of animal waste, plant material, algae cells, or a combination thereof.

3. The method according to claim 1, wherein the sugar or sugar-containing mixture is one or more of a monosaccharide; a disaccharide; a polysaccharide; one or more fresh fruits or vegetables; fruit or vegetable waste; a starch-rich material or a waste thereof; a dairy material containing lactose or a waste thereof; a mixture of any of the above with a suitable solvent; and a mixture thereof.

4. The method according to claim 3, wherein the sugar or sugar-containing mixture is one or more of glucose, fructose, mannose, galactose, sucrose, lactose, maltose, starch, molasses, potatoes, cassava, rice, maize, a mixture of any of the above with a suitable solvent, and a mixture thereof.

5. The method according to claim 1, wherein the inoculum is one or more of *Lactobacillus* sp., *Leuconostoc mesenteroides*, *Lactococcus* sp., and *Aspergillus niger*.

6. The method according to claim 5, wherein the inoculum is one or more of *L. acidophilus*, *L. plantarum*, *L. casei*, *L. pentoaceticus*, *L. bulgaricus*, *L. brevis*, and *L. thermophilus*.

7. The method according to claim 1, wherein the biological material is hydrated.

8. The method according to claim 1, wherein the mixing together of (a) the sugar or a sugar-containing mixture, (b) the inoculum, and (c) the biological material comprises:
   mixing together (a) the sugar or a sugar-containing mixture, (b) the inoculum, and optionally a solvent, to create an acid precursor; and
   mixing the acid precursor with (c) the biological material.

9. The method according to claim 8, wherein the ratio of the amount of acid precursor to the amount of biological material is between about 5 mL:1 g to 20 mL:1 g, based on a dry weight of the biological material.

10. The method according to claim 1, wherein the acid extraction is conducted at a pH in the range of between about 0.1 and about 6.

11. The method according to claim 1, wherein the alkaline solution comprises a base and water.

12. The method according to claim 11, wherein the base is one of NaOH, $Ca(OH)_2$, KOH, $Mg(OH)_2$, and a combination thereof.

13. The method according to claim 11, wherein the base is present in a concentration of about 0.1 M to about 1.0 M.

14. The method according to claim 1, wherein the ratio of the amount of alkaline solution to the amount of biological material is between about 5 mL:1 g to 20 mL:1 g, based on a dry weight of the biological material.

15. The method according to claim 1, wherein the protein extraction is conducted at a pH in the range of between about 11 and about 14.

16. A method for separating phosphorus and protein from biological materials, comprising:
   conducting an acid extraction by mixing together (a) a sugar or a sugar-containing mixture, (b) an inoculum, and (c) a biological material to create a fermentation mixture, then conducting a fermentation process to acidify the fermentation mixture, to produce an acidic supernatant and an acidic precipitate;

separating the acidic supernatant from the acidic precipitate;

conducting a phosphorus precipitation by adding a precipitating composition to the acidic precipitate and mixing the precipitating composition with the acidic precipitate to produce a phosphorus-containing precipitate and a second supernatant;

separating the phosphorus-containing precipitate from the second supernatant;

conducting a protein extraction by adding the second supernatant and an alkaline solution to the acidic supernatant and mixing the second supernatant, the alkaline solution, and the acidic supernatant together to produce a basic supernatant and a basic precipitate;

separating the basic supernatant from the basic precipitate; and recovering an amount of phosphorus from the phosphorus-containing precipitate and recovering an amount of protein from the basic supernatant.

17. The method according to claim 16, wherein the biological material is one of animal waste, plant material, algae cells, or a combination thereof.

18. The method according to claim 16, wherein the acid extraction is conducted at a pH in the range of between about 0.1 and about 6.

19. The method according to claim 16, wherein
wherein the alkaline solution comprises a first base and water, the first base being one of NaOH, $Ca(OH)_2$, and a combination thereof;
wherein the first base is present in a concentration of about 0.1 M to about 1.0 M; and
wherein the protein extraction is conducted at a pH in the range of between about 11 and about 14.

20. The method according to claim 16, wherein the precipitating composition comprises a second base.

21. The method according to claim 20, wherein the precipitating composition further comprises a salt.

22. The method according to claim 20, wherein the precipitating composition further comprises a flocculant.

23. The method according to claim 16,
wherein the precipitating composition comprises a metallic salt containing at least one of calcium, magnesium, iron, and aluminum; and
wherein the amount of the metallic salt is a pre-set amount such that a ratio between the amount of metal and phosphorus in the mixture of the phosphorus precipitation is greater than 0:1 and less than or equal to 3:1.

* * * * *